United States Patent [19]

Lee et al.

[11] Patent Number: 5,215,738

[45] Date of Patent: Jun. 1, 1993

[54] BENZAMIDE AND NICOTINAMIDE RADIOSENSITIZERS

[75] Inventors: William W. Lee, Palo Alto; J. Martin Brown, Stanford; Edward W. Grange, Palo Alto; Abelardo P. Martinez, San Jose, all of Calif.

[73] Assignee: SRI International, Menlo Park, Calif.

[21] Appl. No.: 532,186

[22] Filed: Jun. 1, 1990

Related U.S. Application Data

[63] Continuation of Ser. No. 788,762, Oct. 18, 1985, abandoned, which is a continuation-in-part of Ser. No. 730,761, May 30, 1985, abandoned.

[51] Int. Cl.$^5$ .................... A61K 49/00; A61K 31/44; A61K 31/54
[52] U.S. Cl. ...................... 424/10; 514/355; 514/356; 514/231.2
[58] Field of Search .................. 514/356, 231.2, 355; 424/10

[56] References Cited

U.S. PATENT DOCUMENTS 4,371,540 2/1983 Lee et al. .................... 424/273

FOREIGN PATENT DOCUMENTS 522049 5/1982 Australia.

OTHER PUBLICATIONS

Asquith et al., (1974) Radiation Res. 60:108-118.
Brown et al. (1980) Radiation Res. 82:171-190.
Ben-Hur et al., (1984) Radiation Res. 97:546-555.
Miyakoshi et al., (1985) Radiation Res. 102:359-366.
Jonsson et al., (1985) Cancer Res. 45:3609-3614.
Jonsson et al., (1984) Radiother. and Oncol. 1:349-353.
Calcutt et al., (1970) Br. J. Cancer 24:380-388.
Thraves et al., (1985) Radiation Research 104:119-127.
Lunec et al., (1984) Br. J. Cancer 49, Suppl. VI, pp. 19-25.
Hlavata et al., (1980) Chemical Abstracts 93:112, abstract No. 61755s.
Morisawa et al., (1977) Journal of Medicinal Chemistry 20:129-133.
Brown, *Radiation Research* 64:633-647 (1975).
Brown, *Radiation Research* 72:469-486 (1977).
Kennedy, *Anti-Cancer Drug Design* 2:181-194 (1987).
Brown, "Sensitizers in Radiotherapy," *Medical Radiology: Innovations in Radiation Oncology*, Berlin: Springer-Verlag, 1988.
Chemical Abstracts 105:221854v (1986).
Chemical Abstracts 107:77637y (1987).

*Primary Examiner*—Jerome D. Goldberg
*Assistant Examiner*—Theodore J. Criares
*Attorney, Agent, or Firm*—Dianne E. Reed

[57] ABSTRACT

A method for radiosensitizing hypoxic tumor cells in a warm-blooded animal is provided. The method involves administration of a nicotinamide compound having the structural formula

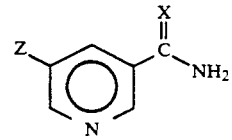

wherein X is O or S, and Z is H, OR, SR or NHR where R is as defined herein. Exemplary compounds for use in conjunction with the disclosed method include: 5-hydroxynicotinamide; 5-hydroxynicotinamide, sodium salt; 5-(2,3-dihydroxypropoxy)nicotinamide; 5-aminonicotinamide; 5-(2-methoxyethylamino)nicotinamide; and 5-acetamidonicotinamide.

5 Claims, 3 Drawing Sheets

BENZAMIDE AND NICOTINAMIDE RADIOSENSITIZERS

REFERENCE TO GOVERNMENT GRANT OR CONTRACT

The invention described herein was made in the course of work under grant or contract from the National Institutes of Health.

CROSS REFERENCE TO RELATED APPLICATION

This application is a continuation of U.S. patent application Ser. No. 06/788,762, filed Oct. 18, 1985, now abandoned, which was a continuation-in-part of U.S. patent application Ser. No. 06/730,761, filed May 30, 1985, also abandoned.

TECHNICAL FIELD

The invention is in the field of radiotherapy. Specifically, it relates to sensitizing tumor cells to radiation using substituted benzamides.

BACKGROUND ART

Hypoxic tumor cell radiosensitizers are compounds that selectively increase the sensitivity of hypoxic cells in tumors to radiation. This specificity for hypoxic cells is important because it is tumors that are typically characterized by such cells. All tumors which are present as solid masses contain these cells, while normal cells generally have an adequate supply of oxygen. The effects of radiation are enhanced by the presence of oxygen, and it is established that as the dose of radiation is increased, the effectiveness of the radiation in destroying target cells is enhanced most dramatically when oxygen is present.

Of course, the use of radiation treatment to destroy tumor cells is only practical if damage to the surrounding normal tissue can be minimized or avoided. The discussion in the foregoing paragraph demonstrates that this is difficult to achieve—normal cells, in view of their oxygen supply, are generally more susceptible to radiation than the target tumor cells. It is therefore desirable to provide a means to sensitize tumor cells, but not the surrounding tissue, to radiation treatment. One mechanism which would permit this is the augmentation of these cells' oxygen supply.

Various heterocyclic compounds, in particular, those with oxidized nitrogen moieties, have been used for the purpose of radiosensitizing tumor cells. Indeed, it has been postulated that the oxidized nitrogen functionality is responsible for this activity. Nitroimidazoles, particularly misonidazole (MIS) and metronidazole have been studied extensively, and MIS is commonly used as a standard in in vitro and in vivo tests for radiosensitizing activity. (See, e.g., Asquith, et al, *Radiation Res* (1974) 60:108–118; Hall, et al, *Brit J Cancer* (1978) 37: 567–569; Brown, et al, *Radiation Res* (1980) 82:171–190; and U.S. Pat. No. 4,371,540. The radiosensitizing activities of certain 1-substituted 3(5)-nitro-s-triazoles and of various quinoxaline-1,4-dioxide derivatives have also been disclosed.

The present invention provides a new group of radiosensitizers that do not contain oxidized nitrogen—the substituted benzamides and nicotinamides and their thio analogs. In this regard, it is important to distinguish the ability to sensitize hypoxic cells selectively, for instance, by enhancing their oxygen supply from another mechanism commonly encountered for "sensitizing" cells—inhibiting the enzyme poly(ADP-ribose)polymerase, which is believed to be essential in the repair of irradiated cells after radiation. This repair mechanism is operative in both hypoxic tumor cells and in normal cells. Hence, administration of "radiosensitizers" which exert their effects by this mechanism does not accomplish the desired purpose of selectively sensitizing the target tumor cells. While lower doses of radiation may be required to kill the tumor, normal cells, too, will experience a higher damage level at this lower dosage. This mechanism, which is called "potential lethal damage repair" (PLDR) can be distinguished experimentally from the desired selective radiosensitization by examining the kinetics of the effect. Since the repair occurs after the radiation is completed, agents which inhibit PLDR must be present during the repair period, and their presence during the irradiation itself is not required. On the other hand, true radiosensitizers must be present during the radiation treatment, and can be removed immediately thereafter, without change in their effect.

Ben Hur, E., et al, *Radiation Res* (1984) 97: 546–555, showed the effect of certain benzamide and nicotinamide derivatives on the repair mechanism in cell culture. Cultures of Chinese hamster ovary cells were used, and the effect of post-irradiation addition of these derivatives on cell survival was studied. It was found that several of these compounds indeed inhibited the repair mechanism, which the authors conclude is therefore relevant to enhancing the killing of those cells by radiation. Miyakoshi, J., et al. *Radiation Res* (1985) 102: 359–366, studied the effects of m-aminobenzamide on the survival, after radiation or hyperthermia, for Chinese hamster cells in culture. The m-aminobenzamide was added either during or after irradiation, and was found to sensitize these cells to the lethal effects of radiation. These cells are not hypoxic, since they are maintained in culture. The Miyakoshi et al results showed that the greatest enhancement ratio was obtained when cells were first treated with X-rays, then at increased temperature in the presence of m-aminobenzamide, followed by prolonged treatment with m-aminobenzamide. These authors also conclude that m-aminobenzamide exerts its effect by interference with the repair mechanism presumably present in all cells.

In vivo studies using nicotinamide were reported by Jonsson, G. G., et al, *Cancer Res* (1985) 45: 3609–3614. In these studies, the repair mechanism was also implicated in the effect of this compound in sensitizing the cells, even though the nicotinamide was administered prior to irradiating. The results obtained by Jonsson et al indicated that the enhancement ratio for the nicotinamide was greater for normal cells in vivo than that exhibited for tumor cells. It is believed that these results were obtained because cells in the normal cell model chosen (tail growth) are atypical of normal cells with regard to their oxygen supply. The authors, however, theorize that treatment with nicotinamide may sensitize cells both as a direct precursor for $NAD^+$ synthesis and as an inhibitor to the repair mechanism. Based on this speculation, the authors suggest that nicotinamide may be useful in sensitizing tumor cells, despite their results to the contrary. Two additional reports on radiosensitization by nicotinamide of tumor cells are those of Jonsson, G. G., et al, *Radiother and Oncol* (1984) 1:

349-353, and of Calcutt, G., et al, *Br J Cancer* (1970) 24: 380-388.

In the invention herein, both benzamide and nicotinamide derivatives and their thio analogs have been shown to have selective radiosensitizing activity in vivo. This effect has been shown to be due to enhancement of oxygen supply and to exhibit a time dependence which corresponds to direct radiosensitazation. Therefore, administration of these compounds prior to radiation is sensitizing selectively for hypoxic (tumor) cells. This is an unexpected property even for those compounds which are known to inhibit poly(ADP-ribose)-polymerase.

DISCLOSURE OF THE INVENTION

The invention provides a valuable addition to the repertoire of compounds available as selective radiosensitizers for hypoxic tumor cells. Some of the compounds useful in this regard are known compounds, others are novel. One aspect of the invention, therefore, is a method of radiosensitizing hypoxic tumor cells in a warm blooded animal comprising administering a compound of the formula:

wherein X is O or S;

Y is H, Me, OMe, OEt, acetoxy or acetamido;

Z is OR, SR or NHR in which R is H, hydrocarbyl (1-6C) including cyclic and unsaturated hydrocarbyl, optionally substituted with 1 or 2 substituents selected from the group consisting of halo, hydroxy, epoxy, alkoxy, alkylthio, amino including morpholino, acyloxy and acylamido and their thio analogs, alkysulfonyl or alkyl phosphonyl, carboxy or alkoxycarbonyl, or carbamyl or alkylcarbamyl, and in which R can optionally be interrupted by a single ether (—O—) linkage; or Z is O(CO)R, NH(CO)R, O(SO)R, or O(POR)R in which R is as above defined. Also, in the compounds of formula 2, Z may be H.

Certain compounds of formulas 1 and 2 wherein Z is in the 3-position, and wherein Z is OR, SR, or NHR in which R is substituted or interrupted with —O—, or wherein Z is O(CO)R, NH(CO)R, O(SO)R or O(POR)R in which R is substituted or interrupted with —O—, are novel. Therefore, in another aspect, the invention is directed to these compounds per se.

MODES OF CARRYING OUT THE INVENTION

A. The Compounds Useful in the Invention

The compounds useful in radiosensitizing hypoxic tumor cells as described herein are derivatives of benzamide or nicotinamide or the thio analogs thereof.

The Benzamide Derivatives

The benzene ring of the benzamide or thiobenzamide of formula 1 may be substituted with one or two additional substituents. The substituent of formula Z is preferably in the 3 position; substituent Y preferentially in position 4. However, if substituent Z is in the 4 position, embodiments wherein Y is in position 3 are preferred. Especially preferred are those embodiments wherein X is O and those wherein Y is H—i.e., the compound of formula 1 is a monosubstituted benzamide.

The hydrocarbyl group represented by R may contain 1-6 carbon atoms, may be saturated or unsaturated, cyclic, or acyclic, and may optionally be interrupted by a single ether linkage. Thus, the unsubstituted form of R can be, for example, methyl, ethyl, n-propyl, s-butyl, n-hexyl, 2-methyl-n-pentyl, 2-ethoxyethyl, 3-(n-propoxy) n-propyl, 4-methoxybutyl, cyclohexyl, tetrahydrofurfuryl, furfuryl, cyclohexenyl, and the like.

R may be substituted with one or two substituents as follows: The halo substituents are fluoro, chloro, bromo, or iodo. The alkoxy substituents represented by OR' and may contain 1 to 4 carbon atoms, and include, for example, methoxy, n-propoxy, and t-butoxy. The amino substituent may be $NH_2$, NHR' or $NR_2'$, where each R' is independently an alkyl of 1-4 carbons or a morpholino. R' may optionally be substituted with 1-2 hydroxy, alkoxy, amino, or halo substituents.

The acyloxy and acylamido groups are represented by R'COO— and R'CONH—, respectively, where R' contains 1-4 carbons, and their athio analogs are represented by R'CSO— and R'CSNH—. Alkyl sulfonyl and alkyl phosphonyl are, respectively, $R'SO_2$ and R'P(OR')O— wherein each R' is independently as above defined. Carboxy is the group —C(O)OH; alkoxycarbonyl is —C(O)OR'; carbamyl is —C(O)$NH_2$; and alkylcarbamyl is —C(O)NHR'.

A particularly preferred subset of benzamide compounds useful in the method of the invention are, in general, those wherein Y is H, Z is in the 3 position, and Z is either hydroxy or contains 4 carbons or less. Where Z is OH, of course, the compounds may also be prepared and used as the pharmaceutically acceptable salts. These salts include those formed from inorganic bases, such as sodium, potassium, or calcium hydroxide, and those formed from organic bases, such as caffeine, ethylamine, and lysine.

Specific particularly preferred compounds include
2-hydroxybenzamide, 3-hydroxybenzamide, and
4-hydroxybenzamide, and their pharmaceutically acceptable salts;
3-methoxybenzamide;
4-ethoxybenzamide;
3-(2-hydroxyethoxy)benzamide, mp 128°-130° C.;
3-(4-acetamido-n-butanoxy)benzamide;
3-[1-(2,3-dihydroxy)propoxy]benzamide, mp 114°-115° C.;
3-[(2-furyl)methylamino]benzamide, mp 125°-126° C.;

3-(2-methoxyethylamino)benzamide, mp 89°-91° C.;
3-(carbethoxymethoxy)benzamide(3-ethoxycarbonyl-methoxybenzamide), mp 158°-159° C.
3-[(2-methoxyethyl)carbamylmethoxy]benzamide, mp 159°-160° C.;
3-[(2-hydroxyethyl)cabamylmethoxy]benzamide, mp 177°-178° C.
3-[1-(2-hydroxy-3-morpholino)propoxy]benzamide
3-(3-amino-n-propoxy)benzamide;
3-(2,3-epoxypropoxy)benzamide;
4-(2,3-epoxypropoxy)benzamide;
4-(3-methoxy-2-hydroxy-n-propoxy)benzamide;
3-(4-ethoxy-3-hydroxy-n-butoxy)benzamide;
3-(3,4-dihydroxy-n-butoxy)benzamide;
4-hydroxy-3-(3,4-dihydroxy-n-butoxy)benzamide;
3-ethoxy-4-(3,4-dihydroxy-n-butoxy)benzamide;
3-hydroxy-4-methoxybenzamide, mp 163°-164° C.;
3-methyl-4-hydroxybenzamide;
4-ethyl-3-methoxybenzamide;
4-methyl-3-(2,3-dihydroxy-n-propoxy)benzamide;
3-methyl-4-(2,3-dihydroxy-n-propoxy)benzamide;
3-methoxy-4-(2,3-dihydroxy-n-propoxy)benzamide;
4-methoxy-3-(2,3-dihydroxy-n-propoxy)benzamide
4-methoxy-3-chloroacetamidobenzamide;
3-chloroacetamidobenzamide;
4-methyl-3-[(2-hydroxyethyloxy)acetamido]benzamide;
3-[(2-hydroxyethyloxy)acetamido]benzamide, mp 118°-119° C.;
2,3-dimethyoxybenzamide;
3,4-dimethyoxybenzamide;
2,3-diethoxybenzamide;
3,4-diethoxybenzamide;
3,5-dimethoxybenzamide;
3,5-diacetamidobenzamide;
3,4-diacetamidobenzamide;
3-propionylbenzamide;
3-(2-acetoxyethoxy)benzamide, mp 121°-122° C.;
4-hydroxy-3-(2-acetoxyethoxy)benzamide;
3-n-hexyloxybenzamide;
3-aminobenzamide;
3-ethylaminobenzamide;
3-(2-methoxyethoxy) benzamide;
3-(2-methoxyethoxy)-4-methylbenzamide;
3-(aminoacetamido)benzamide, mp 139°-140° C.
3-(carbamylmethoxy)benzamide, mp 213°-214° C.
3-(carboxymethoxy)benzamide, mp 251°-252° C.
3-hydroxythiobenzamide, mp 133°-134° C.;
3-(3-ethylsulfonyl)propoxybenzamide;
3-(3-ethylsulfonyl)propylaminobenzamide;
3-(4-methylphosphonyl)-n-butoxybenzamide;
3-(4-diethylphosphonyl)-n-butoxybenzamide;
and the thioamide analogs of the foregoing list of compounds.

In the above list, new compounds which have been identified by conventional spectrographic techniques, elemental analysis, and melting point temperature (mp) are shown with the research mp.

The Nicotinamide Derivatives

The nicotinamide derivatives and their thio analogs contain the substituent Z in the 5-position. Nicotinamide itself (Z=H) is useful in the method of the invention. The preferred embodiments of Z are generally those as set forth above for the benzamide derivatives. Particularly preferred are those embodiments wherein X is O and Z is H, OH, or NH$_2$, or wherein Z contains 4 carbons or less. Those embodiments wherein Z is OH may, of course, be prepared and used as the salts.

Particularly preferred compounds also include: 5-hydroxynicotinamide and its pharmaceutically acceptable salts:
5-methoxynicotinamide;
5-ethoxynicotinamide;
5-(2-hydroxyethoxy)nicotinamide;
5-(4-acetamido-n-butanoxy)nicotinamide;
5-(3-amino-n-propoxy)nicotinamide;
5-(2,3-epoxypropoxy)nicotinamide;
5-(3-acetamidopropoxy)nicotinamide;
5-(3-methoxy-2-hydroxy-n-propoxy)nicotinamide;
5-(4-ethoxy-3-hydroxy-n-butoxy)nicotinamide;
3-(3,4-dihydroxy-n-butoxy)nicotinamide;
5-aminonicotinamide;
5-ethylaminonicotinamide;
5-n-butylaminonicotinamide;
5-(2-methoxyethyl)aminonicotinamide, mp 79°-80° C.;
5-(2,3-dihydroxy)propoxynicotinamide, mp 197°-198° C.;
5-(4-aminobutoxy)nicotinamide;
5-(3-acetamidopropoxynicotinamide;
5-(4-methoxy-n-pentoxy)nicotinamide;
5-(3-chloro-n-propoxy)nicotinamide;
5-(2,3-difluoro-n-propoxy)nicotinamide;
5-(2,3-dibromo-n-hexoxy)nicotinamide;
5-(3-chloroacetamido-n-propoxy)nicotinamide;
5-(2-acetoxyethoxy)nicotinamide
5-(3-acetamido-n-propoxy)nicotinamide;
5-[(2-hydroxyethoxy)acetamido]nicotinamide;
5-[(3-hydroxypropoxy)acetamido]nicotinamide;
5-(3-ethylsulfonyl-n-propoxy)nicotinamide;
5-(3-ethylsulfonyl-n-propylamino)nicotinamide;
5-(4-methylphosphonyl-n-butoxy)nicotinamide;
5-acetamidonicotinamide;
5-(3-hydroxy-n-propoxy)nicotinamide;
5-(4-diethylphosphonyl-n-butoxy)nicotinamide;
and the thioamide analogs of the foregoing list of compounds.

B. Methods of Preparation

Benzamides

Certain of the compounds of formula 1 are available as the benzoic acid analogs. These can be converted to the compounds of the invention by converting the carboxylic acid group to the corresponding amide.

Specifically, for example, 3-hydroxybenzoic acid can be converted to the corresponding 3-hydroxybenzamide by conventional reactions including treatment with SOCl$_2$, followed by reaction with ammonia.

The hydroxy substituent can be further modified by reaction with suitable alkylating or acylating agents. Thus, in general, compounds of formula 1 may be prepared by the reaction The reaction is carried out in the presence of base such as sodium or potassium carbonate in a suitable solvent, preferably an aprotic polar solvent such as dimethylformamide (DMF). The reaction can be carried out at approximately room to elevated temperature. Work-up and purification of products are carried out by conventional means.

To obtain the corresponding compounds of formula 1 wherein Z is NHR, the corresponding reaction using the aminobenzamide starting material is used. Alsi, the presence of the Y substituent in the ring (where the desired component has Y other than H) does not interfere with the general preparation reaction.

It should be recalled that R may contain a substituent and it may then be desirable further to derivatize R. For example, where R contains a free hydroxyl group, the hydroxyl must be protected during the alkylation reaction by, for example, acetylation. The acetyl group may be retained in the compound of formula 1, or may be hydrolyzed to give the corresponding hydroxy compound.

Similarly, R may be obtained as an epoxide substituted alkyl, and the corresponding dihydroxy or alkoxy, hydroxy derivative prepared by hydrolysis.

The thioamide analogs of the invention are prepared by substituting for the benzamide derivative in the reactions set forth above the corresponding thiobenzamide derivatives. These can be obtained from the benzamide derivatives by standard means. In one preferred method the benzamide compound is treated with $P_2S_5$ in dioxane, substantially as described in Edwards, J. T., et al, *Canadian J Chem* (1977) 55:2331.

The compounds of formula 1, therefore, can be prepared from commercially available materials by methods known in the art. The conversions actually employed will, of course, depend on the nature of Y and Z.

Nicotinamides

The 5- substitued nicotinamide derivatives may be prepared using similar reactions. 5-bromonicotinamide may be readily prepared from the corresponding 5-bromonicotinic acid. The 5-bromo substituent may be replaced by either a hydroxyl or an amino group, which groups may then be subsequently alkylated or acylated using the appropriate halides. Thus, the general reaction for preparation for the nicotinamide derivatives which are alkoxy or acyloxy substituted, is as follows:

The general conditions of reaction and necessity for protection in the case of certain embodiments of R is as set forth previously for the benzamide derivatives. Also, analogously, the compounds of the invention wherein the 5- position is substituted by an amino or acylamino group are prepared analogously using the corresponding 5-aminonicotinamide. The thio analogs of the nicotinamide derivatives may be prepared as set forth above for the benzamide derivatives.

In addition, because of the nature of the pyridine ring, the compounds of the invention may be prepared directly from 5-bromonicotinamide by nucleophilic substitution at the 5- position. The reaction is typically carried out in the presence of a base, such as, for example, carbonates or phosphates. A general reaction scheme for the preparation of the compounds of the invention from 5-bromonicotinamide is set forth below:

Alternatively, the corresponding carboxylic acid derivative of the bromo-substituted pyridine can be used as the substrate and subsequently converted to amide.

It is clear that variations of this reaction sequence are possible, as is understood by those in the art. For example, the 5-aminonicotinamide derivative may be first prepared and then converted to the corresponding 5-hydroxy compound.

C. Formulation and Administration

As demonstrated below, the substituted benzamides and nicotinamides and thio analogs of the invention may be used to radiosensitize hypoxic tumor cells in warm-blooded animal hosts. While these radiosensitizers will typically be used in radiotherapy of human patients, they may be used to radiosensitize hypoxic tumor cells in other warm blooded animal species such as other primates, farm animals such as cattle, and sports animals and pets such as horses, dogs, and cats.

Hypoxia is believed to be associated with all types of solid malignant neoplasms. The compounds of the invention may, therefore, be used to radiosensitize neoplastic epithelial cells, endothelial cells, connective tissue cells, bone cells, muscle cells, nerve cells, and brain cells. Examples of carcinomas and sarcomas that may be radiosensitized include carcinomas such as epithelial cell, acidic cell, alveolar cell, basal cell, basal squamous cell, cervical, renal, liver, Hurthle, Lucke, mucinous and Walker, and sarcomas such as Abernathy's, alveolar soft part, angiolithic, botyroid, encephaloid, endometria stroma, Ewing's fascicular, giant cell, lymphatic, Jensen's, juxtocortical osteogenic, Kaposi's, medullary, and synovial. Specific examples of tumors that have been radiosensitized with other radiosensitizers are reported in Adams, G.E., *Cancer: A Comprehensive Treatise* (F. Becker, Ed) vol 6, pp 181–223, Plenum, N.Y., 1977.

The radiosensitizers may be administered to patients orally or parenterally (intravenously, subcutaneously, intramuscularly, intraspinally, intraperitoneally, and the like). It is likely, however, that the preferred route for human administration will be intravenous. When administered parenterally they will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hanks' solution and nonaqueous vehicles such as fixed oils (such as corn, cottonseed, peanut, and sesame), ethyl oleate, and isopropyl myristate. Sterile saline is a preferred vehicle and the compounds are sufficiently water soluble to be made up as a solution for all foreseeable needs. The vehicle may contain minor amounts of additives such as substances that enhance solubility, isotonicity, and chemical stability, e.g., antioxidants, buffers, and preservatives. When administered orally (or rectally) the compounds will usually be formulated into a unit dosage form such as a tablet, capsule, suppository or cachet. Such formulations typically include a solid, semisolid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, aginates, tragacanth, gelatin, syrup, methylcellulose, polyoxyethylene sorbitan monolaurate, methyl hydroxbenzoate, propyl hydroxybenzoate, talc, and magnesium stearate.

The amount of compound administered to the subject is sufficient to radiosensitize the malignant neoplasm to be treated but below that which may elicit toxic effects. This amount will depend upon the type of tumor, the species of the subject being treated, the indication dosage intended and the weight or body surface of the subject. The radiation may be administered to humans in a variety of different fractionation regimes, i.e., the total radiation dose is given in portions over a period of several days to several weeks. These are most likely to vary from daily (i.e., five times per week) doses for up to six weeks, to once weekly doses for four to six weeks. An individual dose of the benzamide, nicotinamide, or thio analog is given before each radiation treatment and is likely to be in the range of 0.01 to 20 mmol/kg and usually in the range of 0.1 to 2 mmol/kg.

Since radiosensitivity is directly related to the concentration of the administered compound in the tumor, the compounds will ideally be administered at a time such that their peak concentration in the hypoxic cells occurs at a predictable time in relation to the time the tumor is exposed to radiation. This time will depend upon the manner in which the compound is administered, the particular dosage form employed, the type of tumor, and the species of the patient. Intravenous administration will typically be done about ½ to about 1 hr prior to radiation exposure to provide maximum radiosensitization. Oral administration may require a somewhat longer lag because the compound must first pass through the gastrointestinal barrier.

EXAMPLES

The following examples further illustrate the compounds of the invention and methods for synthesizing them and using them. These examples are not intended to limit the invention in any manner.

EXAMPLE 1

Preparation of 3-Hydroxybenzamide and 3-Methoxybenzamide

A. Ten g (72.4 mmol) of 3-hydroxybenzoic acid and 10 ml $SOCl_2$ were mixed and allowed to stand for 1 hr, heated on a steam bath for 2 hr, and then cooled and diluted with 25 ml of benzene. The benzene was then evaporated in vacuo to dryness and the residue extracted with 2×50 ml benzene. The extracted residue was dissolved in 25 ml tetrahydrofuran (THF) and this solution added dropwise over a period of 15 min to a stirred, cold (−10° C.) 50 ml solution of concentrated ammonia. The mixture was stirred with cooling for an hour and then at room temperature overnight.

The mixture was poured into an open dish and allowed to evaporate to a solid mass. The solid was triturated with 50 ml ice water, collected, and air dried to yield 6.4 g (64%) of the desired product 3-hydroxybenzamide, mp 160°–162° C. The identity of the product with the desired 3-hydroxybenzamide was further confirmed using thin layer chromatography (TLC).

B. In an analagous manner to that set forth in A, 3-methoxybenzoic acid is converted to the corresponding 3-methoxybenzamide; and the commercially available 3-hydroxy-4-methoxybenzoic acid, 3-methoxy-4-hydroxy benzoic acid, and 3-hydroxy-4-methyl benzoic acid were converted to their corresponding amides.

EXAMPLE 2

Preparation of Thiobenzamides

The 3-hydroxy or 3-methoxybenzamides of Example 1 were treated with $P_2S_5$ as described by Edwards, J. T., et al, *Canad J Chem* (1977) 55:2331, to yield 3-hydroxythiobenzamide, mp 133°–134° C., or 3-methoxythiobenzamide, mp 96°–97° C., respectively.

EXAMPLE 3

Preparation of 3-(2-Acetoxyethoxy)benzamide

A. A mixture of 3-hydroxybenzamide (3.0 g, 21.9 mmol) prepared as in Example 1, 2-bromoethyl acetate (11.9 g, 70.9 mmol), and $K_2CO_3$ (5.7 g, 41.2 mmol) in 40 cc dry dimethyl formamide (DMF) was stirred at 25° C. for 48 hours and filtered. The filtrate was evaporated in vacuo and the resulting residue was recrystallized from 90% $EtOH(H_2O)$ to give 3.2 g (65%) of the desired product as a white crystalline powder, mp 121°–122° C. Here, as in the other examples, the product compound was identified by elemental analysis as well as by IR and mass spectroscopy methods.

B. In a manner analogous to that set forth in ¶ A of this example, but substituting 1-bromo-2,3-epoxypropane for 2-bromoethylacetate, 3-(2,3-epoxy-n-propoxy)benzamide was prepared.

EXAMPLE 4

Preparation of 3-(2-Hydroxyethoxy)benzamide

A. 1.0 g (4.5 mmol) of the 3-(2-acetoxy ethoxy)benzamide prepared in Example 3, ¶ A, was mixed with 2 g Amberlyst 15 and 50 ml methanol. The mixture was stirred for 40 hr and filtered. The filtrate was evaporated in vacuo to dryness and the residue dissolved in 50 ml absolute ethanol and filtered to remove a small amount of insoluble material. The filtrate was evaporated in vacuo to obtain 750 mg of the white solid 3-(2-hydroxyethoxy)benzamide, representing 92% yield.

The identity of the desired product was confirmed by TLC and elemental analysis: Calculated for $C_9H_{11}NO_3$; C: 59.65; H: 6.11; N: 7.73; Found: C: 59.56; H: 6.05; N: 7.70.

B. In an analogous manner, but effecting lysis of the epoxide ring in the 3-(2,3-epoxy-n-propoxy)benzamide of Example 3, ¶ B, using aqueous solution, dimethylamine, morpholine, methanol, or ethyl mercaptan, the corresponding compounds of the invention—3-(2,3-dihydroxy-n-propoxy)benzamide, 3-(3-(N,N-dimethylamino)-2-hydroxy-n-propoxy)benzamide, 3-(3-morpholino-2-hydroxy-n-propoxy)benzamide, 3-(3-methoxy-2-hydroxy-n-propoxy)benzamide, and 3-(3-ethylthio-2-hydroxy-n-propoxy)benzamide—are prepared.

EXAMPLE 5

Preparation of 3-(Ethoxycarbonylmethoxy) benzamide

The subject compound was prepared using the general method of Example 3, except that 10.0 g (72.9 mmol) of 3-hydroxybenzamide was reacted with 29.0 g (236.6 mmol) of ethyl chloroacetate and 19.0 g (137.5 mmole) of $K_2CO_3$ in the presence of 150 cc dry DMF. There was obtained 11.8 g (72%) of the desired product having an mp of 158°–159° C.

EXAMPLE 6

Preparation of 3-[(2-Methoxyethyl)carbamylmethoxy]benzamide and Other Oxy- and Aminocarbonyl Derivatives A. A mixture of 3-(ethoxycarbonylmethoxy) benzamide (1.00 g, 4.5 mmol), 2-methoxyethylamine (0.9 g, 11.5 mmole) and MeOH (20 cc) was stirred at 25° C. for 40 hours. The product 3-[(2-methoxyethyl)carbamylmethoxy]benzamide was collected by filtration and recrystallized from isopropanol to give the desired compound (0.6 g, 53%) as a white crystalline solid, mp 159°–160° C.

B. In a similar manner, but substituting for 2-methoxyethylamine, ammonia, aqueous base, or 2-hydroxyethylamine, the desired products, 3-carbamylbenzamide, mp 213°–214° C., 3-carboxybenzamide, mp 251°–252° C., and 3-(2-hydroxyethylcarbamyl)benzamide, mp 177°–178° C., are, respectively, obtained.

EXAMPLE 7

Preparation of 3-[(2-Furfuryl)methylamino]benzamide

A mixture of 3-aminobenzamide (0.5 g, 3.67 mmol), 2-furfural (0.53 g, 5.51 mmol), and EtOH (4 cc) was stirred at 25° C. for 2 hours. The reaction mixture was then cooled to 0° C., treated with sodium borohydride (0.2 g, 5.34 mmol), and stirred for 16 hours as the temperature was allowed to rise to 25° C. EtOAc (50 cc) and $H_2O$ (1 cc) were added, the mixture was filtered, and the phases were separated. The organic phase was evaporated in vacuo and the residue was purified by chromatography on silica gel using $Et_2O$:EtOAc (10:1) to give 0.45 g (57% of the desired compound as a white crystalline solid, mp 125°–126° C.

EXAMPLE 8

Preparation of 3-(2-Methoxyethylamino) benzamide 10 g of 3-aminobenzamide and 30 g of rainy nickel were mixed with 150 ml of 2-methoxy ethanol and refluxed for 15 hours. (Molar ratio of aminobenzamide:solvent = 1:26.) Celite was added to the reaction mixture and the debris removed by filtration. The filtrate was then evaporated under reduced pressure and the product, 3-(2-methoxyethylamino)benzamide crystallized on cooling, mp 89°–91° C.

EXAMPLE 9

Preparation of 3-aminoacetamidobenzamide

A portion of 1,1'-carbonyldiimidazole (CDI) (813 mg, 5.01 mmol) was added to a stirred solution of Cbz-protected glycine (807 mg, 3.85 mmol) in THF (10 ml). The solution was stirred at 25° C. for 1 hour and cooled to −10° C. Water (200 mg) was added, followed by 3-aminobenzamide (500 mg, 3.67 mmol). Stirring was continued at −10° C. for ½ hour and then at 25° C. for 16 hours, during which the intermediate protected aminoacetamidobenzamide precipitated. The white solid was collected by filtration, combined with 5% PD/C (50 mg) in glacial HOAc (10 ml) and placed under hydrogen (40 psi) with agitation for 4 hours. The mixture was filtered, the filtrate evaporated in vacuum to dryness and recrystallized with ethyl ether/methanol to obtain 340 mg (48%) of the title compound, mp 139°–140° C.

EXAMPLE 10

Preparation of 3-(2-hydroxyethoxyamido) benzamide

Chloroacetyl chloride (4 g, 35.4 mmol) was added to a stirred mixture of 3-aminobenzamide (4.0 g 25.9 mmol), $K_2CO_3$ (22 g, 159 mmol), water (40 ml), and dioxane (40 ml) at 0° C. The reaction mixture was stirred at 0° C. for 1 hour and 25° C. for 16 hours, resulting in a solid precipitate. The precipitate was collected, washed, and dried to yield 4.1 g (75%) of the desired 3-chloroacetamidobenzamide, mp: 210 (D).

The 3-chloroacetamidobenzamide (11.62 g, 54.65 mmol) was combined with a solution containing 87.5% KOH (4.5 g, 7 mmol), water (4.5 ml), and ethylene glycol (113 ml). Mixture was heated at 90° C. for 1.5 hours, cooled to room temperature, neutralized with 1N HCl, and diluted this ethanol (100 ml). The resulting suspension was filtered, the filtrate evaporated in vacuo, and the residue purified on silica gel and recrystallized in acetone/ether to obtain 5.5 g (42%) of the desired title compound, mp 118°–119° C.

EXAMPLE 11

Preparation of 5-Bromonicotinamide

Twenty g (99.0 mmol) of 5-bromonicotinic acid in 80.0 ml $SOCl_2$ was heated for 5 hr at 85°–90° C. and evaporated to dryness at 50° C. under reduced pressure to afford 21.57 g (98.8% yield) of the acyl halide; mp 70°–73° C., compared with the literature, mp 74°–75° C. (Graf, R., J Prakt Chem (1933) 138: 244).

All of the 5-bromonicotinoyl chloride prepared above was dissolved in 100 ml hot 1,2-dimethyoxyethane and added slowly during about 15 min to 500 ml cold, concentrated $NH_4OH$ in a 1 l round-bottom flask. The mixture was then stirred 1.5 hr at −10° C. to about 5° C. followed by filtration to collect white crystalline plates of 5-bromonicotinamide which were dried at 56° C. for 1.0 min to afford 17.79 g (89.2% yield) mp 222°–223° C. (lit. 224°–225° C., Czuba, W., *Rec Trav Chim* (1963) 82: 988–996; lit 141°–142° C., Morisawa, Y., *J Med Chem* (1977) 20: 129).

EXAMPLE 11

Preparation of 5-(2-Methoxyethylamino) nicotinamide

A. One g (4.97 mmol) of the 5-bromonicotinamide, 1 g (5.0 mmol) of $K_2CO_3$, 0.31 g (1.25 mmol) of $CuSO_4.5H_2O$, and 5 ml of: 2-methoxyethylamine in a stainless steel bomb was heated 1.5 hr in an oil bath at 110°–120° C. The reaction mixture was cooled and diluted with 25 ml $CH_2Cl_2$ and treated with excess solid NaHS and $H_2S$ gas, then filtered through a celite pad. The residues were washed with $CH_2Cl_2$. The filtrates were concentrated to semi-dryness and chromatographed through a 45 cc Florisil column packed in $CH_2Cl_2$.

Fractions 13–17, eluted with 325 ml EtOAc afforded 0.28 g (29% yield) of 5-(2-methoxyethylamino) nicotinamide, mp 79°–80° C. Analysis (calculated: C 55.3, H 6.71, N 21.50; found: C 55.4, H 6.88, N 21.47). MS: 195.

B. Alternatively, a mixture of 1 g (4.95 mmol) of 5-bromonicotinic acid, 1 g of $CuSO_4 5H_2O$, and 5 g 2-methoxyethylamine in a stainless steel bomb was heated 2.5 hr in an oil bath at 100°–110° C. The reaction mixture was cooled, diluted with 25 ml MeOH, and evaporated to dryness at 55° C. under reduced pressure. The green residue was mixed with 40 ml MeOH, saturated with anhydrous HCl at room temperature, and allowed to stand 2 days in a stoppered flask, then evaporated to dryness. The residue was mixed in 125 ml $CH_2Cl_2$ and treated with 7 g $Na_2CO_3$ in 25 ml $H_2O$ and mixed throughly. The $CH_2Cl_2$ solutions were decanted, dried over $Na_5SO_4$, and evaporated to afford 0.86 g (83% yield) of the intermediate, 5-(2-methoxy ethylamino) nicotinic acid, methyl ester. The ester was reacted in a bomb with $NH_3$/MeOH and chromatographed to afford an overall yield of 32% of pure 5-(2-methoxyethylamino)nicotinamide.

EXAMPLE 13

Preparation of 5-Aminonicotinamide and Its Salt

To a magnetically stirred portion of 280 ml concentrated $NH_4OH$ in a stainless steel bomb at room temperature was added 50 g (0.2475 mol) of 5-bromonicotinic acid in small additions of about 2–3 g each. The solution was then treated with 20 g of CuO and the stirred reaction mixture was heated 18 hr in an oil bath at 150°–160° C. The reaction was then worked up by the method of Urban (*Helv Chim Acta* (1964) 47: 363) to afford 40.67 g (94% yield) of 5-aminonicotinic acid HCl. The crystalline free base product was obtained by the acidification of a basic solution of 5-aminonicotinic acid (in NaOH) to pH 5.3 to afford 21 g (61.4% yield); mp 304°–305° C. dec (lit. 295°–296° C. dec; Urban, supra).

A mixture of 2.2 g (15.9 mmol) of 5-amino nicotinic acid in 50 ml MeOH was saturated with anhydrous HCl and heated 3 hr at reflux employing a dry ice finger condenser. The solution was evaporated to dryness and the residue was dissolved in 50 ml MeOH and saturated with $NH_3$ gas in a stainless steel bomb. The bomb was heated 20 hr at 120° C. (oil bath temperature). the reaction mixture was evaporated to dryness and the residue was mixed with 15 g $NaHCO_3$ and 25 ml MeOH, then chromatographed through a 150 cc $SiO_2$ (70–230 mesh) column packed in EtOAc and eluted with 20% MeOH/EtOAc to afford 1.81 g (81% yield) of 5-amino nicotinamide; IR(N) 3430m-s, 3100m-s, 1680s, 1630s.

A portion of 5-aminonicotinamide was dissolved in 50 ml MeOH (very soluble) and the solution was saturated with anhydrous HCl to afford the crystalline precipitate of 5-aminonicotinamide.HCl, 1.05 g (55% yield), mp 263°–264° C.

EXAMPLE 14

Preparation of 5-Hydroxynicotinamide and Its Salt

A mixture of 4.00 g (29.0 mmol) of 5-aminonicotinic acid in 400 ml of 0.1N $H_2SO_4$ at room temperature was diazotized with 2.2 g (31.8 mmol) of $NaNO_2$ by the method of R. Graf (supra) to afford 5-hydroxynicotinic acid. The intermediate free acid was esterified in anhydrous methanolic HCl by the method of Urban (supra) to afford 2.34 g (53% overall yield) of 5-hydroxy nicotinic acid, methyl ester, mp 186°–187° C. (lit 182°–193° C.; Urban, supra). The IR data gave the characteristic 5-hydroxy band at 2550.

A mixture of 2 g (13.06 mmol) of the methyl ester in 80 ml MeOH was saturated with gaseous $NH_3$ at 0° C., then heated 16 hr in a stainless steel bomb in an oil bath at 125° C. The reaction mixture was evaporated to dryness. The residue was dissolved in 2-methoxyethanol at reflux temperature, filtered through celite, and evaporated to dryness leaving a white solid. The solid was triturated with cold IPA-MeOH, 1:1, then dried to afford 1.35 g (74.8% yield) of the 5-hydroxynicotinamide, mp 275°–276° C.

Analysis (calculated: C 52.2, H 4.38, N 20.28; found: C 52.3, H 4.64, N 19.91). MS: 195 (4).

The sodium salt was prepared from the free acid. The salt is very water soluble and has an mp >300° C.

EXAMPLE 15

Preparation of 5-(2,3-Dihydroxypropoxy) nicotinamide

A mixture of 0.4 g (2.0 mmol) of the above sodium salt in 10 ml ethanol and 10 ml 2-methoxyethanol was treated with 2 ml glycidol and heated about 2 hr on a steam bath. The reaction mixture was filtered and the filtrates were diluted with ether to afford 0.4 g (73% yield) of 5-(2,3-dihydroxypropoxy)nicotinamide in two crops, mp 197°–199° C.

IR(N): 3300 bd s, 3180 bd s, 1675 s, 1570 s.

EXAMPLE 16

Preparation of 5-Acetamidonicotinamide

A mixture of 4 g (28.96 mmol) of 5-aminonicotinic acid, 35 ml $Ac_2O$, and 2 ml $CF_3CO_2H$ in a stainless steel bomb was heated 22 hr at 125° C. (oil bath temperature). The reaction mixture was evaporated to dryness at 55° C./20 mm pressure and 55° C./1 mm pressure. The gummy residues were mixed with methanol and again evaporated to dryness. The residues were mixed with 50 ml concentrated $NH_4OH$, allowed to stand about 2 hr at room temperature, and evaporated to dryness at 60° C. under reduced pressure. The residues were mixed with 25 ml ethanol and again evaporated to dryness. The residue afforded a light beige crystalline material upon trituration with warm ethanol. The solid product was collected and dried to afford 4.55 g (80% yield) of 5-acetamidonicotinic acid, ammonium salt.

IR(N): 3115 sh, m-s, 1670 s, 1560 bd, s (salt).

The above salt is converted to the desired nicotinamide derivative by conversion to the methyl ester and then to the corresponding amide.

EXAMPLE 17

In Vivo Assay for Radiosensitization Activity

The compounds of the invention are tested in vivo for radiosensitization activity by the assay of Brown, J. M. *Radiation Res* (1975) 64:633-47, incorporated herein by reference. For this assay EMT6 tumors in female BALB/c mice weighing 20-25 g are used. These mice are bred under specific pathogen-free conditions and are 3-4 months old at the beginning of each experiment. The EMT6 tumor is grown intradermally in the flank from an inoculation of $2 \times 10^5$ tumor cells taken from the 2nd-8th in vitro passage of the tumor cells since removal from the previous in vivo tumor. Two tumors per mouse are implanted, and are used as subject tumors when they reach a volume of approximately 100 ml. At this point the tumors contain approximately 20% hypoxic cells.

Figure 1:
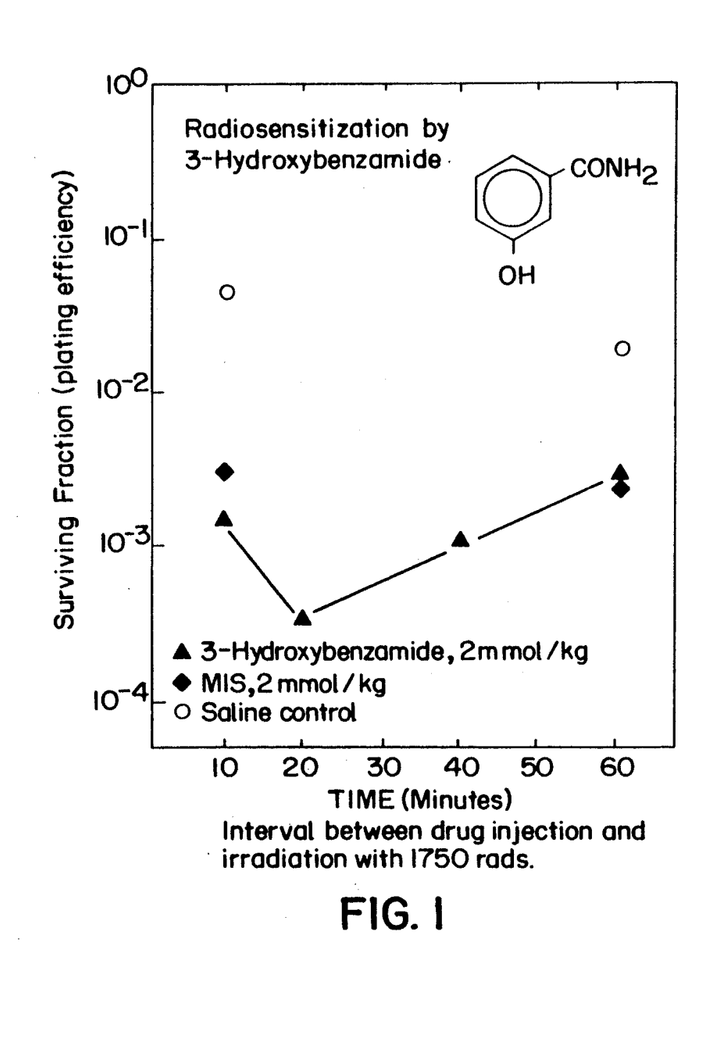
FIG. 1 shows the radiosensitizing effect of 3-hydroxybenzamide as compared to MIS.
Figure 2:
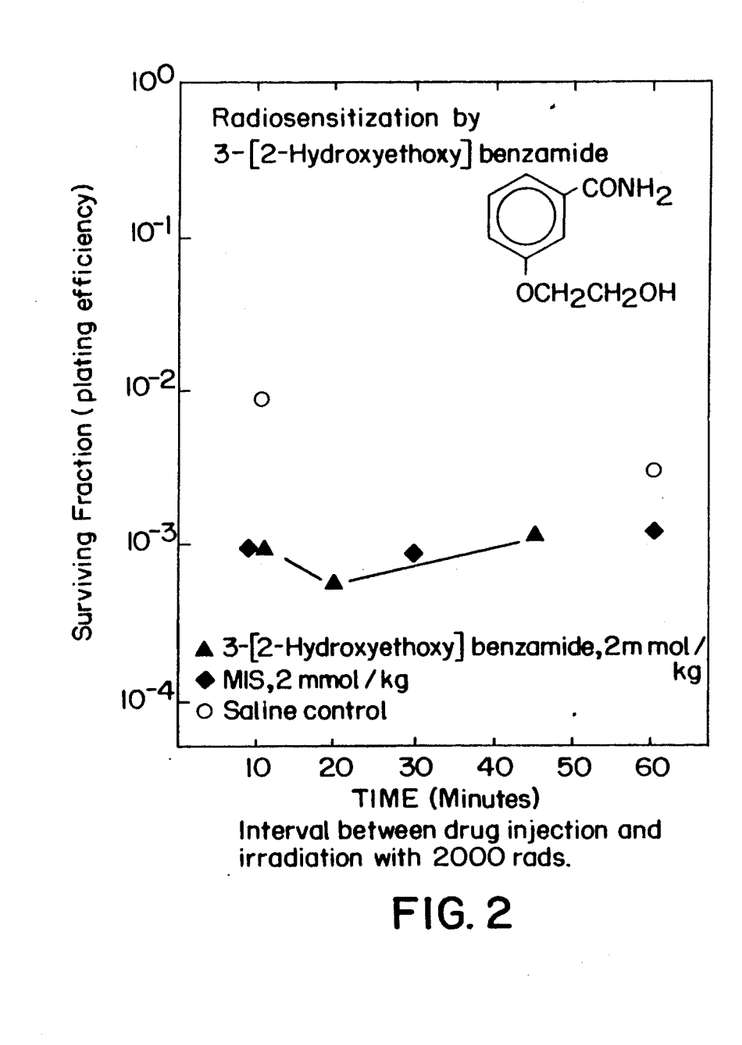
FIG. 2 shows similar results for 3-(2-hydroxyethoxy)-benzamide.
Figure 3A:
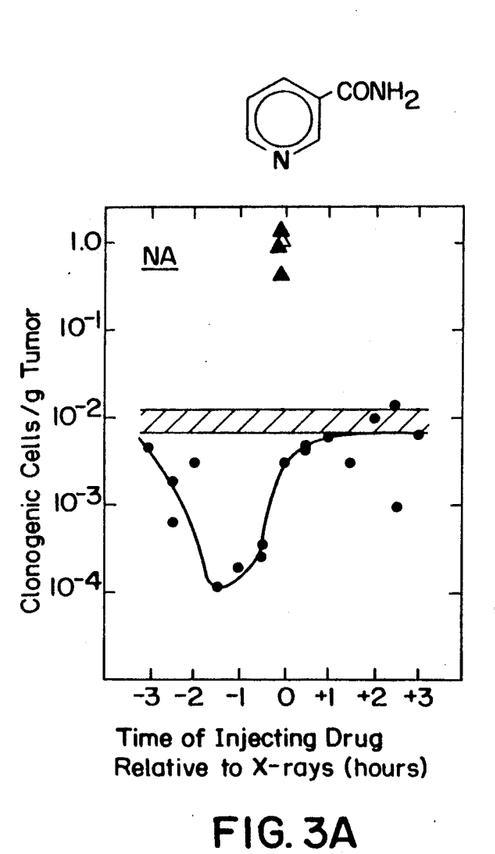
FIG. 3A-3C and 4A-4C show the dependence of the radiosensitizing effect of several nicotinamide derivatives on time of injection.
Figure 3B:
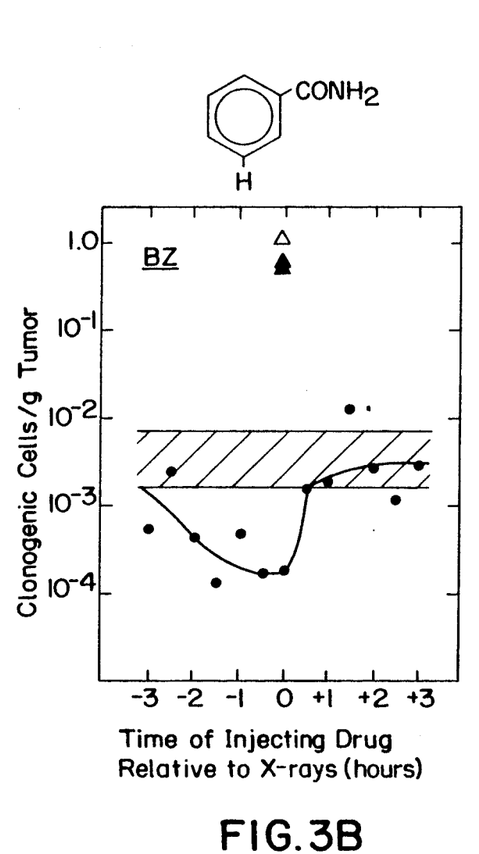
Figure 3C:
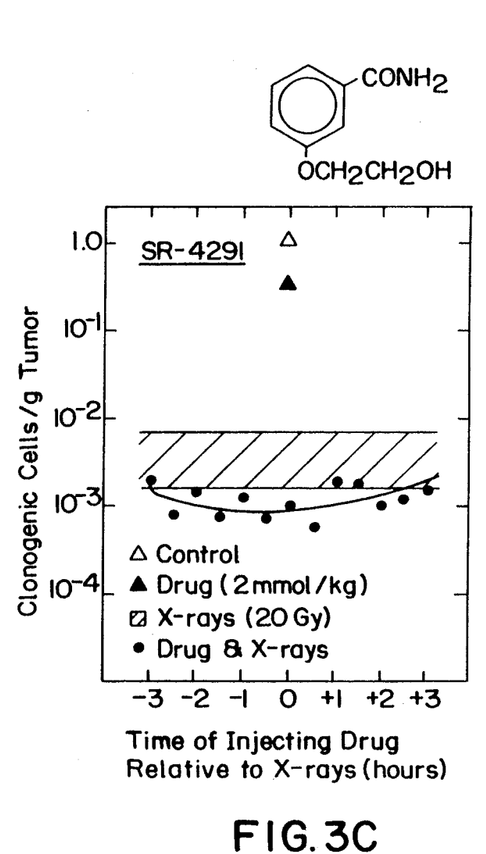
Figure 4A:
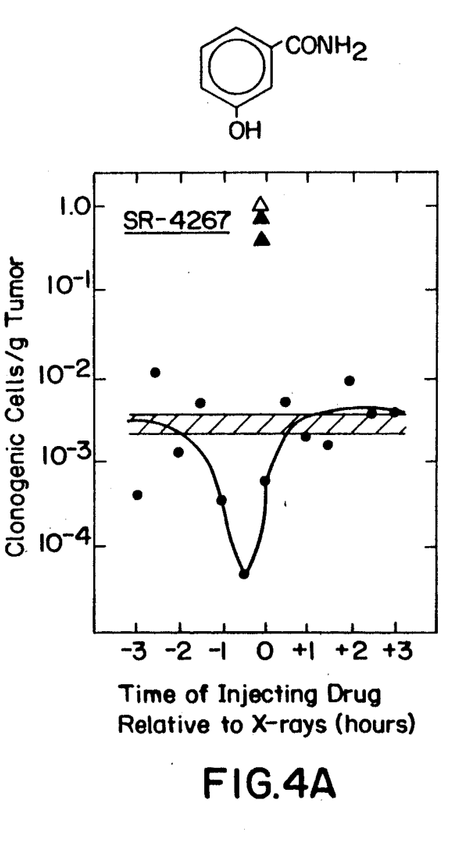
Figure 4B:
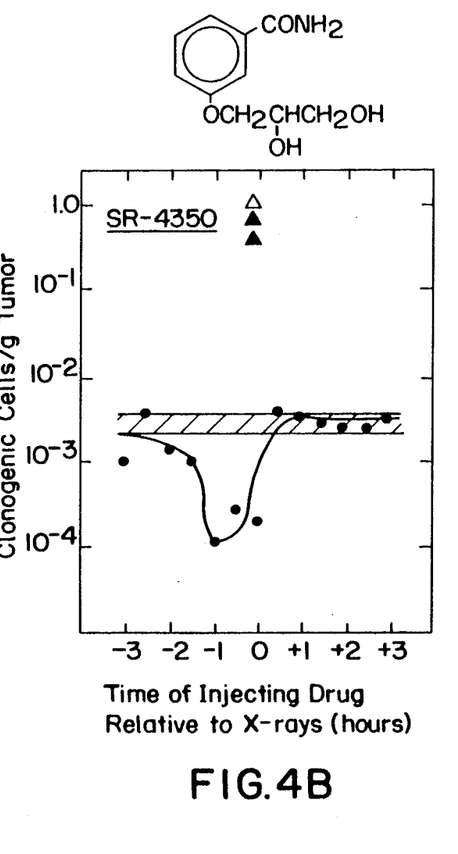
Figure 4C:
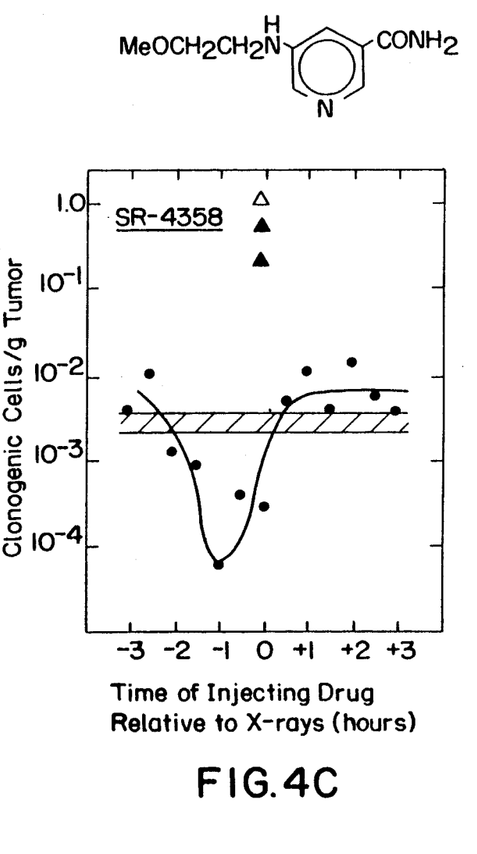

Test compounds are compared against MIS in this assay. The test compound is tested at a fixed injected dose of either 5 mmol/kg or ⅔ of the $LD_{50}$ (whichever is lower), MIS is injected into controls at the same dose. Additional suitable controls of test compound-injected but nonirradiated and saline-injected and irradiated mice are also included. A fixed radiation dose of 2,000 rad is applied at variable intervals of 5 min to 2 hr between injection and irradiation. Typically, irradiation is applied at 5, 10, 15, 20, 30, 45, 60, 90, and 120 min following intraperitoneal administration of both drugs. By using these intervals, the results give an indication of both the optimum time to irradiate and of how the test compound sensitizes in relationship to MIS. The results of such time-course experiments using 3-hydroxybenzamide and 3-(2-hydroxyethoxy)benzamide are shown in FIGS. 1 and 2, respectively.

Irradiation of the EMT6 tumors is done by irradiating nonanesthetized tumor-bearing mice in a Plexiglas box. Irradiation conditions are 250 kVp X-rays, 15 mA, FSC 33 cm, added filtration of 0.35 mm Cu, half value layer 1.3 mm Cu, and a dose rate of 317 rad/min.

Radiosensitization activity is judged by survival rate of dissected and cultured tumor cells as follows: The tumor-bearing mice are killed immediately after irradiation, and tumors dissected from the skin, cut into several pieces, and made into a fine brei by high-speed chopping with a razor blade attached to a jigsaw. The brei is added to 30 ml of Hank's buffered salt solution (HBSS) containing 0.02% DNase, 0.05% promase, and 0.02% collagenase. The suspension is stirred for 30 min at 37° C., filtered, and centrifuged at 1,600 rmp for 10 min at 4° C. The cell pellet is resuspended in complete Waymouth's medium plus 12-½% horse serum plus 2-12% fetal calf serum (FCS) and an aliquot mixed with trypan blue and counted with the use of a hemacytometer. Suitable dilutions of this serum plated into 60- or 100-mm polystyrene petri dishes (Lux Scientific Corp) in 5 or 15 ml of medium. After incubation for 13 days, the colonies are fixed and stained, and those containing 50 cells or more are counted. The dilution yielding an average count of 25-100 colonies in a 60 mm dish is used in calculation of results. The more highly diluted the sample to achieve this result, the less successful the killing and the less sensitizing the test compound.

The test compound is scored on the scale of 0 to 4 based on how it compares with MIS. The scoring system is:

0: No radiosensitization
1: Minimal radiosensitization (some radiosensitization relative to controls but lowest survival > 3 × lowest survival with MIS)
2: Moderate radiosensitization (not good as MIS, but lowest surviving fraction < 3 × lowest surviving fraction with MIS)
3: Good radiosensitization (equal to MIS)
4: Excellent radiosensitization (superior to MIS)

EXAMPLE 18

Cytotoxicity Tests

Cytotoxicity tests were also carried out on some of the compounds. The test procedure was as follows: Log-phase Chinese hamster ovary HA-1 cells were trypsinized (0.5% trypsin in Hank's buffered salt solution (HBSS)) and plated in 60 mm Permanox petri dishes in concentrations necessary to yield approximately 30 colonies after experimental treatment. The cells were allowed to attach overnight. Then the medium was removed from each dish and replaced with 2 ml of medium containing varying concentrations of the test compound. The petri dishes were then placed in nylon chamber fitted with gassing ports and, to achieve hypoxia, were gassed at room temperature with humidified $N_2$ containing 5% $CO_2'$ for 1 hr at a rate of 1 l/min. The cells are then exposed to 10 mM of the test compound for 1 hr at 22° C. The % cell survival is read after such treatment.

EXAMPLE 19

Determination of $LD_{50}$ $LD_{50}$ is determined in BALB/c female mice (weighing 20-25 g) following intraperitoneal (ip) injection, unless the compound tested has low lipophilicity and is very soluble, wherein intravenous (iv) administration is used. Whichever is used, the radiosensitization and pharmacokinetic assays are performed using the same route of administration. $LD_{50}$ values at 1, 2, 5, and 60 days are determined by administering graded doses of the drug dissolved in physiological saline immediately prior to injection.

EXAMPLE 20

Results

The results of the assay of Examples 4 and 5 are as follows:

| Compound | Cytotoxicity % Cell Survival | Radio-sensitization |
|---|---|---|
| nicotinamide | | 3 |
| 3-(2-methoxyethylamino) nicotinamide | | 3 |
| 3-hydroxybenzamide | 90, 77 | 3 |
| 3-(2-hydroxyethoxy)benzamide | 89 | 3 |

In the sensitivity assay of Example 17, each of the compounds of the invention tested gave a sensitizer enhancement ratio of 1.6 at a 1-2 mM concentration, which is comparable to that for MIS. In addition, these compounds were shown to have no radiosensitizing activity in normal cells.

Modifications of the above described modes for carrying out the invention that are apparent to those of skill in the chemical, pharmaceutical, medical, and related arts are intended to be within the scope of the following claims.

We claim:

1. A method to destroy hypoxic tumor cells in a warm-blooded animal, which method comprises:
   (a) administering to said warm-blooded animal a compound of the formula:

wherein X is O or S;
Z is H, OR, SR or NHR in which R is H, hydrocarbyl (1-6C) including cyclic and unsaturated hydrocarbyl, optionally substituted with 1 or 2 substituents selected from the group consisting of halo, hydroxy, epoxy, alkoxy, alkylthio, amino including morpholino, acyloxy and acylamido and their thio analogs, alkylsulfonyl or alkylphosphonyl, carboxy or alkoxycarbonyl, or carbamyl or alkylcarbamyl, and in which R can optionally be interrupted by a single ether (—O—) linkage; or Z os O(CO)R, NH(CO)R, O(SO)R, or O(POR)R in which R is as above defined, in an amount effective to radiosensitize said hypoxic tumor cells, (b) followed by, after a time period to provide maximum radiosensitization, irradiating said tumor cells with a dose of radiation effective to destroy said cells.

2. The method of claim 1 wherein Z is OH or $NH_2$.

3. The method of claim 1 wherein the compound is selected from the group consisting of:
   5-hydroxynicotinamide;
   5-hydroxynicotinamide, sodium salt;
   5-(2,3-dihydroxypropoxy)nicotinamide;
   5-aminonicotinamide;
   5-(2-methoxyethylamino)nicotinamide; and
   5-acetamidonicotinamide.

4. The method of claim 1 wherein X is O.

5. The method of claim 1 wherein X is S.

* * * * *